United States Patent [19]
Jinotti

[11] 4,193,406
[45] Mar. 18, 1980

[54] DUAL PURPOSE CATHETER

[76] Inventor: Walter J. Jinotti, 10 Scott St., New Brunswick, N.J. 08901

[21] Appl. No.: 943,387

[22] Filed: Sep. 18, 1978

[51] Int. Cl.² ............................................. A61M 25/00
[52] U.S. Cl. ................................ 128/204.18; 128/240; 128/276; 128/274; 128/204.24; 128/205.19
[58] Field of Search ................. 128/240, 241, 276–278, 128/350, 351, 145.5, 274; 137/625.68

[56] References Cited

U.S. PATENT DOCUMENTS

| | | | |
|---|---|---|---|
| 1,214,941 | 2/1917 | Morris et al. | 128/145.5 |
| 2,291,563 | 7/1942 | Rotter et al. | 137/625.68 |
| 2,812,765 | 11/1957 | Tofflemire | 128/276 |
| 4,036,210 | 7/1977 | Campbell et al. | 128/240 X |

*Primary Examiner*—Dalton L. Truluck
*Attorney, Agent, or Firm*—Robert A. Green

[57] ABSTRACT

The disclosure is of a catheter including a first suction tube, a second oxygen supply tube, and valve means for alternately connecting the proper tube to suction or oxygen whereby mucous can be removed from a body and then oxygen can be fed to the body.

9 Claims, 5 Drawing Figures

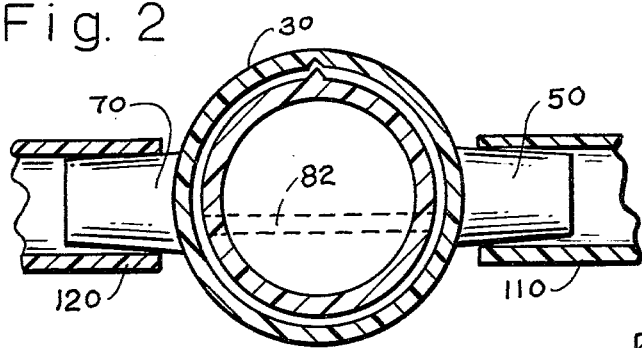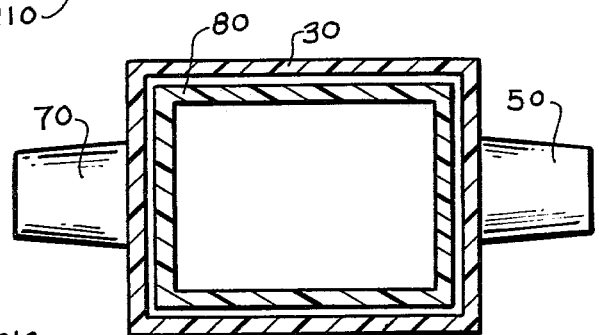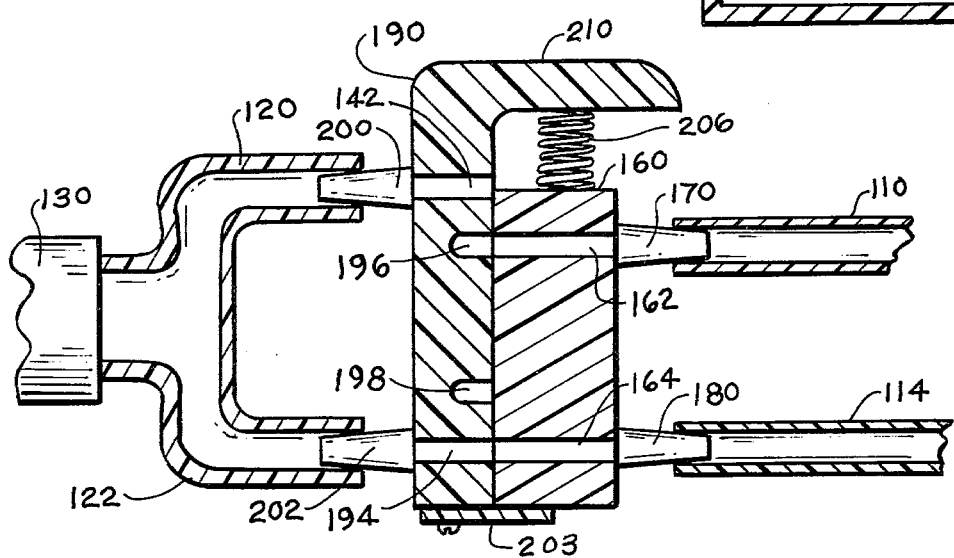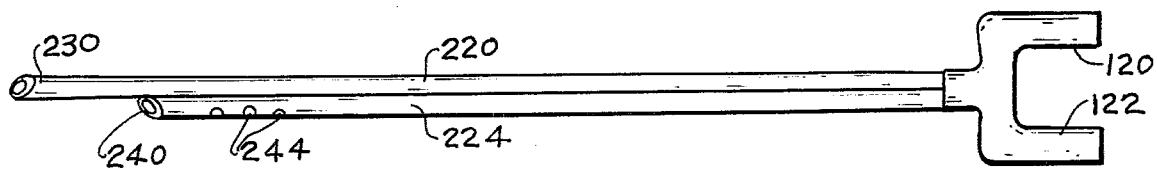

DUAL PURPOSE CATHETER

BACKGROUND OF THE INVENTION

There are many medical situations, such as after accidents or surgery, when it is necessary to perform suctioning to remove fluids from the lungs. During such a procedure, the blood may show a drop in the levels of gases, including oxygen, which is an undesirable condition. In the past, it has been customary to perform a suction operation, discontinue the suction operation to permit oxygen levels to restore, resume suctioning, etc. This is a time-consuming, and not a medically effective, procedure. The present invention provides apparatus which can perform alternate suctioning and oxygenating in an efficient and medically effective manner.

DESCRIPTION OF THE DRAWINGS

FIG. 2 is a sectional view along the lines 2—2 in FIG. 1;

FIG. 3 is a sectional view, similar to FIG. 2, showing a modification of the invention;

FIG. 4 is a sectional, elevational view of a modification of the invention; and

FIG. 5 is a side elevational view of a modification of a portion of the invention.

DESCRIPTION OF THE PREFERRED EMBODIMENTS

Figure 1:
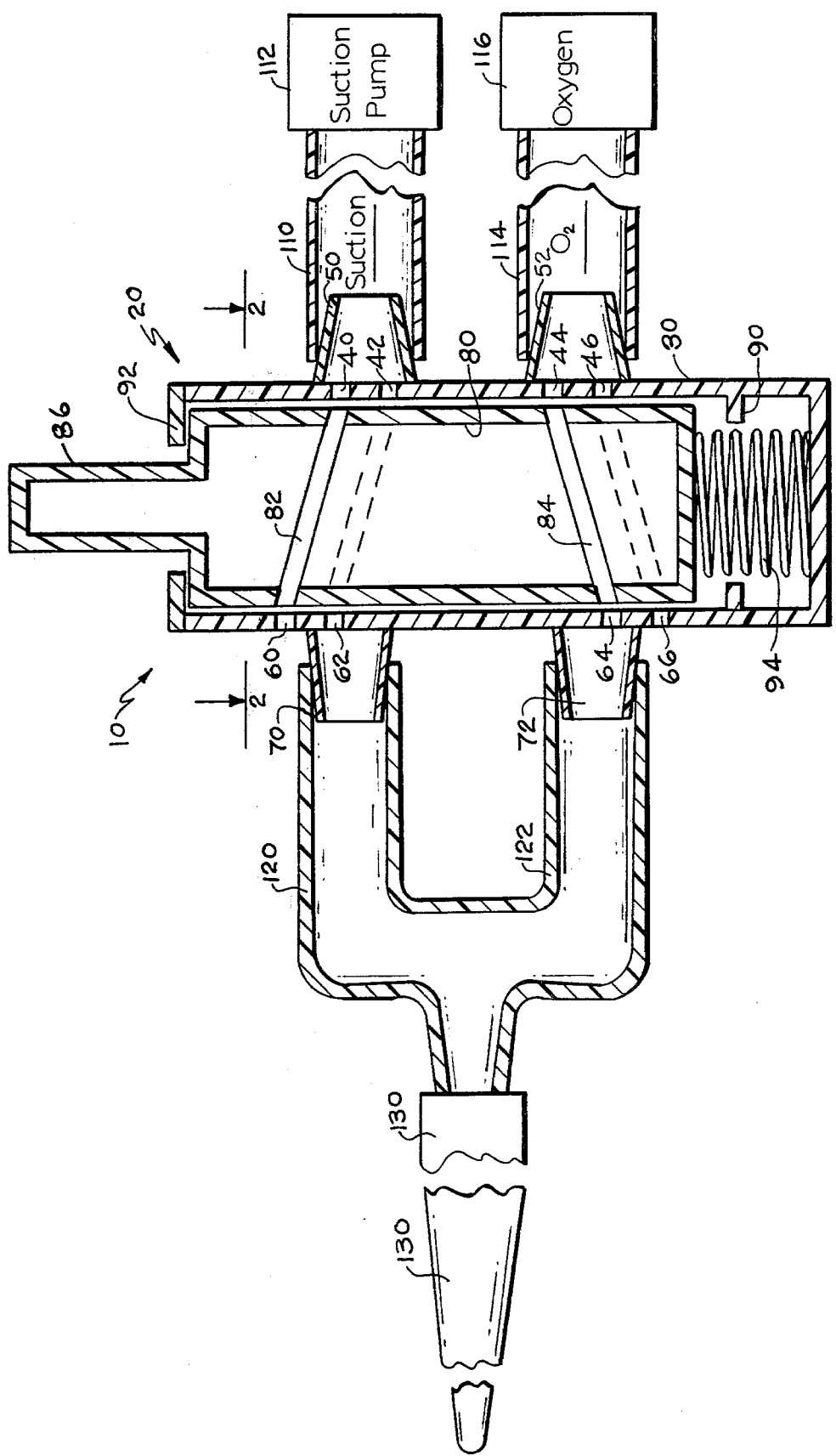
FIG. 1 is a sectional, elevational view of the invention.

Referring to FIG. 1, the apparatus of the invention 10 includes a valve mechanism 20 including, in one embodiment, a first outer tube 30 having a closed end 32 and an open end 34. The first tube has, along one longitudinal axis, two upper holes 40 and 42 and two lower holes 44 and 46. A first nozzle 50 is attached to the outer surface of the first tube covering the two upper holes 40 and 42, and a second nozzle 52 is attached to the outer surface of the tube covering the second two holes 44 and 46. Similarly, on the opposite surface of the first tube 30 and aligned along a common longitudinal axis are two upper holes 60 and 62 and two lower holes 64 and 66, with a third nozzle 70 covering only the lower 62 of the two upper holes and a fourth nozzle 72 covering only the upper hole 64 of the two lower holes. It is noted that the two holes 60 and 62 are not axially aligned with the two holes 40 and 42, but rather are at a slightly higher level, and, similarly, the two holes 64 and 66 are slightly lower than the two holes 44 and 46, for a purpose to be described.

A second inner tube or cylinder 80 is slidably mounted in the first tube 30. The second tube has two through-holes, or through-passages, 82 and 84, and, if the tube is solid, the through-holes are drilled or otherwise formed therein, and, if the tube is hollow, then the through-holes may be lengths of tubing. The first or upper through-hole 82 slants downwardly to the right, and the second lower through-hole 48 slants upwardly to the right, as seen in FIG. 1.

The inner tube or valve 80 is adapted to occupy two positions, in one of which, shown in solid lines in FIG. 1, the upper hole 82 communicates at its left end with the hole 60 and the atmosphere and at its right end with the hole 40 and nozzle 50; and the lower hole 84 communicates at its left end with hole 64 and nozzle 72 and at its right end with the hole 44 and nozzle 52. The valve 80 is adapted to be moved downwardly to occupy a second position shown by the dash line representation of the holes 82 and 84 in which the upper hole 82 communicates with the hole 42 and nozzle 50 and with hole 62 and nozzle 70, and the lower hole 84 communicates between hole 66 and the atmosphere at its left end and hole 46 and nozzle 52 on the right.

For convenience, dash lines are shown only for holes or passages 82 and 84 although, of course, the entire tube 80 would occupy the operating upper and lower positions.

One arrangement for controlling these movements of the tube 80 utilizes an annular stop 90 formed on the inner surface of outer tube 30 to set the lower limit of the downward movement of tube 80 at which holes 82 and 84 occupy the dash line positions. An upper annular stop 92 is secured to the upper open end of tube 30 to set the limit of the upward movement of the tube 80 to the required upper position, at which the holes 82 and 84 occupy the positions represented by the solid lines. A spring 94 is located inside tube 30 and bears against the closed lower end of tube 80 to urge tube 80 to its upward position.

Tube 80 carries a push button 86 at its upper end.

The outer tube and inner tube may be rectangular in cross-section (FIG. 3), or they may be circular in cross-section (FIG. 2), in which case, some anti-rotation means is provided, for example, a longitudinal V-shaped notch 100, in the inner surface of the outer tube 30, in which is positioned a corresponding V-shaped longitudianl projection 102 on the outer surface of the inner tube 80.

To complete the apparatus 10, a tube 110 is coupled between nozzle 50 and a suction source 112, and a tube 114 is connected between nozzle 52 and a source of oxygen 116. In addition, an assembly 118, including a tube 120, a tube 122, and a single tube or catheter 130, is provided. Tube 120 is coupled at one end to nozzle 70, tube 122 is coupled at one end to nozzle 72, and both tubes 120 and 122 are joined together at their opposite ends and to a single tube or catheter 130 which is inserted in the body of a patient being treated.

In operation of the invention and the apparatus 10, the single catheter tube 130 is inserted in the trachea of an individual, and, with the sliding valve 80 pushed to the lower position, the dash line positions of the through-holes 82 and 84 are operative, and the suction source 112 is connected to the catheter 130 and mucous is removed from the body. Then, when desired, the sliding valve 80 is elevated so that the through-holes occupy the solid line positions, and, in this orientation thereof, the suction source 112 is removed from the catheter 130 and oxygen is fed through the tubes 114 and 122 into the catheter 130 and to the body. The slide 80 may be moved up and down to alternate the suction and oxygen-feeding operations, as required.

A modification of the invention shown in FIG. 4 includes a valve block 160 having first and second through-holes 162 and 164, one hole 162 connected to a nozzle 170 which is connected by tube 110 to suction source 112, and the other hole 164 connected to a nozzle 180 which is connected by tube to source of oxygen 116. A sliding member 190 is mounted in air-tight engagement with the rear surface of the block 160 and is provided with upper and lower through-holes or passages 192 and 194, respectively, and first and second air holes 196 and 198, respectively, which communicate with the atmosphere. The through-holes 192 and 194 are coupled to first and second nozzles 200 and 202 which are coupled to the rear assembly 118 shown in FIG. 1 of tubes 120 and 122 and the single catheter 130. A stop plate 203 is secured to the lower surface of slide 190 to set the upper limit of movement of the slide.

The slide 190 is biased upwardly by means of a spring 206 disposed between the handle 120 and the block 160 and in the upward position of the slide which is set by plate 203, the lower holes 164 and 194 are aligned, and the upper air hole 196 is aligned with the upper hold 162 in the block. With this alignment, the air hole 196 is connected through hole 162 and nozzle 170 to suction, and oxygen is fed through the aligned holes 164 and 194 to the nozzle 102 and catheter 130 to the body. If the slide 190 is depressed, with its movement limited by handle 210, the upper two holes 162 and 192 are aligned and the catheter 130 is connected to suction and the oxygen is connected through the hole 164 and air hole 198 to the atmosphere.

In a modification of the invention shown in FIG. 5, the rear assembly 118 of FIG. 1, including the single catheter 130 and the two tubes 120 and 122, is removed and replaced by apparatus 214 comprising two lengths of flexible tubing 220 and 224 which are secured together to form a unitary assembly. The tubes 220 and 224 form a double-lumen catheter, and they are designed so that they can be readily inserted into the trachea. The first tube 220, which is considered to be the suction catheter, has an open lower end 130 through which fluids are suctioned. The opposite end of tube 220 comprises tube 120 of assembly 118.

The second tube 224 is the oxygen catheter, and it has an open lower end 240 which is adjacent to but does not extend to the lower end 230 of the suction catheter 220. One or more auxiliary openings 244, through which oxygen can flow into the body, are provided in tube 224 near open end 240. The lower end of the oxygen catheter 224 is spaced about one inch or so from the lower end 230 of the suction catheter 220 to effectively separate the lower functioning ends of the two tubes. Thus, the suctioning and oxygenating functions can be performed separately and without interfering with each other.

In operation of this modification of the invention, having the apparatus of FIGS. 1 and 5 combined, the lower end of the assembly 214 of tubes 220 and 224 is inserted into the trachea. Then, by operating the valve 80 to the proper position, suction force is applied and the desired suction operation is performed. After a suitable time, the valve 80 is operated to decouple the suction and to couple the oxygen catheter 224 to the oxygen which is fed into the body. Again, after a time, the functions are reversed by operating the valve 80. Of course, assembly 214 could be coupled to the proper portion of the apparatus of FIG. 4.

The various parts of the apparatus of the invention may be made of metal or plastic as desired, and the various tubes are flexible or rigid as required. Such details can be left to those skilled in the art to provide.

What is claimed is:

1. A dual-purpose catheter comprising
an elongated tube having an insertion end and a valve connection end, said insertion end adapted for coupling to the human body and said valve connection end adapted for alternate connection to a source of suction or a source of oxygen.

adjustable valve means connected to said valve connection end and disposed between said tube and said sources of suction and oxygen,
said valve means including therein first and second through-passage means, said first through-passage means being adapted to be disposed (1) in a first position in which it is connected between said suction source and said tube and (2) in a second position in which it is connected between the environment and said suction source, and, when said first through-passage means is in said first position, said second through-passage means is in a first position in which it is connected between the atmosphere and said source of oxygen and, when said first through-passage means is in said second position, said second through-passage means is connected between said tube and said source of oxygen.

2. The apparatus defined in claim 1 wherein said valve means includes a tube having two pairs of holes, a first upper pair and a second lower pair aligned on a longitudinal axis and a second pair of holes, a third upper pair and a fourth lower pair aligned on the opposite longitudinal axis,
said third pair of holes being offset upwardly above said first pair of holes, said fourth pair of holes being offset downwardly below said second pair of holes,
a first nozzle covering said first pair of holes,
a second nozzle covering said second pair of holes,
a third nozzle covering the lower hole of said third pair of holes,
a fourth nozzle covering the upper hold of said fourth pair of holes,
a first passage means between the upper holes of said first and third pairs of holes and adapted to be moved to be disposed between the lower holes of said first and third pairs of holes, and
a second passage means between the upper holes of said second and fourth pairs of holes and adapted to be moved to the lower holes of the second and fourth pairs of holes.

3. The apparatus defined in claim 2 wherein said valve means includes an outer tube and a slidable inner tube disposed within said outer tube, said outer tube carrying said first, second, third and fourth pairs of holes, and said inner tube carrying said first and second passage means.

4. The apparatus defined in claim 2 and including a spring in said first tube and urging said second tube upwardly out of said first tube, a first stop means in said first tube to limit the downward movement of said inner tube, and a second stop means at the upper end of said first tube to limit the upward movement of said inner tube.

5. The apparatus defined in claim 3 wherein said first and second tubes have rectangular cross-sections.

6. The apparatus defined in claim 3 wherein said first and second tubes have circular cross-sections and a mating notch and projection combination to prevent rotation of the second tube with respect to the first tube.

7. The apparatus defined in claim 1 wherein said valve means includes
a first block having a first through passage means for connection to suction and a second through passage means for connection to oxygen,
a slidable block positioned adjacent to said first block and having third and fourth through passage means for connection to said tube, said slidable block also having fifth and sixth passage means to the atmosphere, said slide being adapted to occupy (1) a first position in which said second and fourth passage means are aligned and said first and fifth passage means are aligned and (2) a second position in which said first and third passage means are aligned and said second and sixth passage means are aligned.

8. The apparatus defined in claim 1 wherein said tube assembly comprises first and second tubes coupled at one end to said valve means and coupled together at their other ends to a single catheter.

9. The apparatus defined in claim 1 wherein said tube assembly includes (1) a first suction catheter having one end coupled to said valve means and the other remote end adapted to be inserted in the body and (2) a second oxygen catheter having one end coupled to said valve means and its other remote end adapted to be inserted in said body but not extending as far as the remote end of the suction catheter, said suction catheter and oxygen catheter being secured together as an unitary assembly.

* * * * *